(12) United States Patent
Green et al.

(10) Patent No.: US 8,190,234 B2
(45) Date of Patent: May 29, 2012

(54) MOVABLE PATIENT SUPPORT WITH SPATIAL LOCATING FEATURE

(75) Inventors: Charles A. Green, Holbrook, NY (US); Mark Gelbien, Levittown, NY (US); John Greenhalgh, Greenlawn, NY (US)

(73) Assignee: Fonar Corporation, Melville, NY (US)

( * ) Notice: Subject to any disclaimer, the term of this patent is extended or adjusted under 35 U.S.C. 154(b) by 1693 days.

(21) Appl. No.: 11/172,519

(22) Filed: Jun. 30, 2005

(65) Prior Publication Data

US 2005/0285595 A1     Dec. 29, 2005

Related U.S. Application Data

(63) Continuation-in-part of application No. 09/918,369, filed on Jul. 30, 2001, now Pat. No. 7,697,971.

(60) Provisional application No. 60/252,837, filed on Nov. 22, 2000, provisional application No. 60/222,098, filed on Jul. 28, 2000.

(51) Int. Cl.
*A61B 5/00*     (2006.01)

(52) U.S. Cl. ........ 600/415; 324/307; 600/410; 600/414; 5/601

(58) Field of Classification Search ............. 600/410, 600/414, 415, 417, 424; 606/130; 324/307–309; 382/128; 5/601
See application file for complete search history.

(56) References Cited

U.S. PATENT DOCUMENTS

| | | |
|---|---|---|
| 4,105,923 A | 8/1978 | Hynes, Jr. |
| 4,534,076 A | 8/1985 | Barge |
| 4,534,358 A | 8/1985 | Young |
| 4,608,991 A | 9/1986 | Rollwitz |
| 4,613,820 A | 9/1986 | Edelstein et al. |
| 4,629,989 A | 12/1986 | Riehl et al. |
| 4,651,099 A | 3/1987 | Vinegar et al. |
| 4,668,915 A | 5/1987 | Daubin et al. |
| 4,707,663 A | 11/1987 | Minkoff et al. |
| 4,766,378 A | 8/1988 | Danby et al. |
| 4,777,464 A | 10/1988 | Takabatashi et al. |
| 4,829,252 A | 5/1989 | Kaufman |
| 4,875,485 A | 10/1989 | Matsutani |
| 4,968,937 A | 11/1990 | Akgun |

(Continued)

FOREIGN PATENT DOCUMENTS

EP     0067933     12/1982

(Continued)

OTHER PUBLICATIONS

Supplementary European Search Report, EP 04 81 2587.

*Primary Examiner* — Brian Casler
*Assistant Examiner* — Amanda Lauritzen
(74) *Attorney, Agent, or Firm* — Lerner, David, Littenberg, Krumholz & Mentlik, LLP

(57) ABSTRACT

A magnetic resonance imaging system having a patient support arranged for pivoting movement about a pivot axis and linear or sliding motion along a support axis transverse to the pivot axis is provided with a device for measuring the location of a patient feature to be imaged. The measured location is used to define coordinates for positioning the patient support. These coordinates desirably are used to automatically move the patient support from a loading position to an imaging position where the feature will be properly aligned with the field axis of the imaging magnet. The system simplifies patient positioning.

32 Claims, 8 Drawing Sheets

U.S. PATENT DOCUMENTS

| | | | |
|---|---|---|---|
| 4,985,678 A * | 1/1991 | Gangarosa et al. | 324/318 |
| 5,008,624 A | 4/1991 | Yoshida | |
| 5,061,897 A | 10/1991 | Danby et al. | |
| 5,065,761 A | 11/1991 | Pell | |
| 5,085,219 A | 2/1992 | Ortendahl et al. | |
| 5,124,651 A | 6/1992 | Danby et al. | |
| 5,150,710 A | 9/1992 | Hall et al. | |
| 5,153,546 A | 10/1992 | Laskaris | |
| 5,162,768 A | 11/1992 | McDougall et al. | |
| 5,194,810 A | 3/1993 | Breneman et al. | |
| 5,197,474 A | 3/1993 | Englund et al. | |
| 5,207,224 A | 5/1993 | Dickinson et al. | |
| 5,210,893 A | 5/1993 | Uosaki et al. | |
| 5,221,902 A | 6/1993 | Jones et al. | |
| 5,229,723 A | 7/1993 | Sakurai et al. | |
| 5,250,901 A | 10/1993 | Kaufman et al. | |
| 5,291,890 A | 3/1994 | Cline et al. | |
| 5,305,749 A | 4/1994 | Li et al. | |
| 5,315,276 A | 5/1994 | Huson et al. | |
| 5,382,904 A | 1/1995 | Pissanetzky | |
| 5,412,363 A | 5/1995 | Breneman et al. | |
| 5,436,607 A | 7/1995 | Chari et al. | |
| 5,490,513 A | 2/1996 | Damadian et al. | |
| 5,519,372 A | 5/1996 | Palkovich et al. | |
| 5,525,905 A | 6/1996 | Mohapatra et al. | |
| 5,565,834 A | 10/1996 | Hanley et al. | |
| 5,592,090 A | 1/1997 | Pissanetzky | |
| 5,606,970 A | 3/1997 | Damadian | |
| 5,680,861 A | 10/1997 | Rohling | |
| 5,681,326 A | 10/1997 | Lax et al. | |
| 5,735,278 A | 4/1998 | Hoult et al. | |
| 5,825,843 A | 10/1998 | Kobayashi | |
| 5,926,876 A | 7/1999 | Haigh et al. | |
| 5,983,424 A * | 11/1999 | Naslund | 5/601 |
| 6,003,174 A | 12/1999 | Kantrowitz et al. | |
| 6,094,760 A | 8/2000 | Nonaka et al. | |
| 6,249,695 B1 | 6/2001 | Damadian | |
| 6,279,579 B1 | 8/2001 | Riaziat et al. | |
| 6,288,546 B1 | 9/2001 | Damadian et al. | |
| 6,356,081 B1 | 3/2002 | Misic | |
| 6,385,481 B2 | 5/2002 | Nose et al. | |
| 6,456,075 B1 | 9/2002 | Damadian et al. | |
| 6,496,007 B1 | 12/2002 | Damadian et al. | |
| 6,504,371 B1 | 1/2003 | Damadian et al. | |
| 6,534,982 B1 | 3/2003 | Jakab | |
| 6,675,037 B1 | 1/2004 | Tsekos | |
| 6,677,753 B1 | 1/2004 | Danby et al. | |
| 6,806,712 B2 | 10/2004 | Akgun | |
| 6,828,792 B1 | 12/2004 | Danby et al. | |
| 6,934,574 B1 | 8/2005 | Damadian et al. | |
| 6,986,179 B2 | 1/2006 | Varadharajulu et al. | |
| 7,123,008 B1 * | 10/2006 | Damadian et al. | 324/309 |
| 7,239,906 B1 | 7/2007 | Green et al. | |
| 2003/0204136 A1 * | 10/2003 | Green et al. | 600/415 |
| 2004/0030241 A1 | 2/2004 | Green et al. | |
| 2004/0138553 A1 | 7/2004 | Damadian | |
| 2005/0187459 A1 * | 8/2005 | Trequattrini et al. | 600/415 |
| 2005/0222505 A1 | 10/2005 | Damadian et al. | |
| 2005/0285595 A1 | 12/2005 | Green et al. | |
| 2006/0173278 A1 | 8/2006 | Wahl et al. | |
| 2008/0161676 A1 | 7/2008 | Satragno et al. | |

FOREIGN PATENT DOCUMENTS

| | | |
|---|---|---|
| EP | 0350267 | 1/1990 |
| JP | 1305937 | 12/1989 |
| JP | 2001104276 | 4/2001 |
| SE | 9302066 | 12/1994 |
| WO | 01/70109 | 9/2001 |

* cited by examiner

MOVABLE PATIENT SUPPORT WITH SPATIAL LOCATING FEATURE

CROSS-REFERENCE TO RELATED APPLICATIONS

This application is a continuation-in-part of U.S. patent application Ser. No. 09/918,369, filed on Jul. 30, 2001, which claims the benefit of the filing dates of U.S. Provisional Patent Application Nos. 60/252,837, filed Nov. 22, 2000 and 60/222,098, filed Jul. 28, 2000. The disclosures of all of the aforementioned applications and patents are hereby incorporated herein by reference.

FIELD OF THE INVENTION

The present invention relates to magnetic resonance imaging.

BACKGROUND OF THE INVENTION

In magnetic resonance imaging, the patient must be positioned within a large magnet which provides a strong, uniform magnetic field. While the patient is positioned in the magnetic field, radiofrequency excitation signals are applied so as to elicit magnetic resonance signals. Magnetic field gradients are applied so as to affect the magnetic resonance process and thereby spatially encode the magnetic resonance signals. An image of the patient can be reconstructed from the resulting magnetic resonance signals. Because magnetic resonance imaging provides unique imaging capabilities and freedom from risks associated with other imaging modalities, it is a valuable tool for physicians.

The requirement that the patient be positioned within the magnet, however, poses unique challenges in magnetic resonance imaging. For optimum imaging, the feature of the patient's body to be imaged must be aligned with that portion of the patient-receiving space within the magnet where the magnetic field has optimum properties, commonly referred to as the imaging volume. Many magnetic resonance imaging instruments are solenoidal instruments in which the magnet is a large cylindrical structure having a horizontal central bore and coils surrounding the central bore, so as to provide an imaging volume at a particular axial location along the central bore. These instruments typically are provided with a slidable bed which can be moved into and out of the central bore in a motion like that of a common desk drawer. In this case, the instrument can be built with a laser or other marker disposed at a fixed axial distance from the axial location of the imaging volume. The technician can slide the bed until the feature to be imaged is aligned with the marker. When the feature is aligned with the marker, the feature is located at the known axial distance from the axial center of the imaging volume. Thus, after aligning the feature with the marker, the technician need only slide the bed through this known axial distance. The technician may do this manually, or by entering a command into a computer associated with the apparatus to actuate a drive mechanism. Alternatively, the apparatus can be arranged to move the bed through the known axial distance in response to a button push or other input from the technician indicating that the feature has been aligned with the marker.

Instruments of this type, however, suffer from numerous drawbacks. They provide an intensely claustrophobic experience for the patient. They are unable to accommodate extremely obese patients or patients with bulky casts or other appliances affixed to them. Moreover, they can provide images of the patient only while the patient is disposed with the long axis of his or her body horizontal, i.e., in a recumbent or prone position.

Certain apparatus disclosed in the aforementioned patents and applications, substantially overcomes these drawbacks. Such apparatus provides a magnet with a pair of pole structures such as ferromagnetic poles, superconducting coils, permanent magnets, or resistive coils disposed along a horizontal axis referred to herein as the polar axis or magnetic field axis. A patient-receiving gap is defined between the pole structures. The patient support, which may include an elongated platform, is mounted for compound movement to a variety of imaging positions. Typically, the apparatus includes a carriage which is mounted on guides such as rails for movement along a horizontal axis, referred to herein as the carriage axis, transverse to the magnetic field axis. A support structure is mounted to the carriage for pivoting movement relative to the carriage about a pivot axis. The pivot axis typically is horizontal and parallel to the field axis. The patient support is also mounted for sliding movement along the support structure so that the patient support can move along a support axis transverse to the pivot axis. Typically, the patient support includes an elongated platform extending in directions parallel to the support axis. The patient support may also include a footrest projecting from the platform at one end or a seat projecting from the platform. Drive mechanisms are provided for moving the carriage along the carriage axis, pivoting the support structure and patient support about the pivot axis and sliding the patient support along the support axis.

Systems of this type provide extraordinary versatility for the imaging process. The patient may be imaged in a substantially upright position, as, for example, while standing on the footrest and leaning against the platform; in a recumbent position, lying on the platform with the platform generally horizontal; or in any intermediate position, as, for example, a Trendelenberg or reverse-Trendelenberg position, with the platform disposed at an oblique angle to the horizontal. Moreover, systems of this type provide extraordinary ease of use. The patient support may be disposed in a load position, with the platform extending generally vertically, and the patient may be positioned on the support while the support is in this load position, as, for example, by simply sitting down on the seat or standing on the footrest and leaning against the patient support. After the patient is positioned on the support, the technician actuates the apparatus to tilt the support frame and hence the patient support to an appropriate angle, move the carriage and slide the support along the support axis so as to bring the patient support to a position where the patient is disposed at the desired orientation relative to gravity, and with the feature to be imaged disposed within the imaging volume.

However, prior to the present invention, this process has been performed by trial and error, with the technician adjusting the position of the patient support in the various degrees of freedom by entering appropriate commands into the computer which controls the drive mechanisms. This process can be time-consuming. Moreover, the technician may not accurately position the feature of interest. This, in turn, requires repositioning and restarting the imaging process.

SUMMARY OF THE INVENTION

One aspect of the present invention provides an improved magnetic resonance imaging system. A system according to this aspect of the present invention desirably includes a magnet defining a patient-receiving space and an imaging volume within the patient-receiving space. For example, the magnet may include opposed pole structures disposed along a field axis extending through the imaging volume, as discussed above. The system according to this aspect of the invention desirably includes structures such as a carriage defining a pivot axis and also includes a patient support defining a support axis transverse to the pivot axis, the patient support being pivotable about the pivot axis through a range of rotational locations and movable relative to the pivot axis along the support axis through a range of support axis locations. Typically, the carriage, and hence the pivot axis, are also movable along a carriage axis transverse to the field axis. The apparatus most preferably includes a locating device which is arranged to determine a position of a feature of a patient's body while the patient is supported on the patient support. The apparatus desirably includes a computer arranged to provide a set of locations including a rotational location specifying the angle at which the support structure and patient support are tilted about the pivot axis, and a support axis location specifying the location of the patient support in the direction of the patient support. The set of locations defines an imaging position at which the feature of the patient's body is disposed within the imaging volume. The set of locations is based at least in part on the measured location of the feature of the patient's body. Where the carriage is movable along the carriage axis, the set of locations desirably includes a carriage-axis location as well.

The locating device may be arranged to determine the position of the patient's body feature relative to the patient support or relative to the support structure. Most preferably, the locating device is arranged to determine the position of the feature in a direction parallel to the support axis. For example, the locating device may include a scale mounted to the patient support or support structure so that the technician can determine the position of the body feature by visual comparison to the scale. Alternatively or additionally, the measuring device may include a pointer or other device slidable along the patient support or support structure and an electrical or other transducer for determining the location of the pointer.

The locating device also may be arranged to determine the location of the feature of the patient's body in an offset direction which is perpendicular to the pivot axis and which is also perpendicular to the support axis, and the computer may be operative to calculate the set of locations based, in part, on this determined location in the offset direction. Typically, the offset direction is perpendicular to the plane of the platform constituting the patient support.

In another variant, the apparatus may include a fixture mountable on the patient support for supporting a feature of the patient at a known location in the offset direction, and the computer may be arranged to calculate the set of locations based in part on this known location. A plurality of different fixtures may be provided, as, for example, leg rests, head rests, arm rests and the like. In yet another arrangement, the computer may be operative to calculate the set of locations based in part on an assumed location of the feature of the patient in the offset direction, as further discussed below. Most commonly, the rotational position is specified by the operator to meet a particular patient need, as, for example, an upright, recumbent or Trendelenberg position, and the computer is operative to calculate the set of locations based, in part, on this specified position.

Systems according to this aspect of the invention can provide rapid and precise positioning of the patient; once the patient is loaded on the support and the position of the body feature has been measured, the technician need only input this information into the system and command the system to position the patient in the imaging position.

A further aspect of the invention provides methods of positioning a patient for magnetic resonance imaging. The methods according to this aspect of the invention desirably include the step of loading a patient on a patient support while the patient support is disposed in a load position, and then specifying an imaging position for the patient by measuring the position of a feature of the patient's body after the loading step and automatically calculating a set of locations defining an imaging position based at least in part on the measured position of the body feature, so that movement of the patient support to the imaging position will align the body feature with the field axis and imaging volume. The methods according to this aspect of the invention desirably include moving the patient support from the load position to the imaging position by rotating the patient support about a pivot axis parallel to the field axis and moving the patient support linearly relative to the pivot axis along a support axis transverse to the pivot axis, and the step of specifying an imaging position most preferably includes specifying a rotational position and a support axis position. Methods according to this aspect of the invention can provide benefits similar to those discussed above in connection with the apparatus.

Still other aspects of the invention provide similar positioning in systems which incorporate patient supports having fixed rotational orientation as, for example, in systems which include plural patient supports each adapted to position the patient in a different orientation.

These and other objects, features and advantages of the present invention will be more readily apparent from the detailed description set forth below, taken in conjunction with the accompanying drawings.

DETAILED DESCRIPTION

Figure 1:
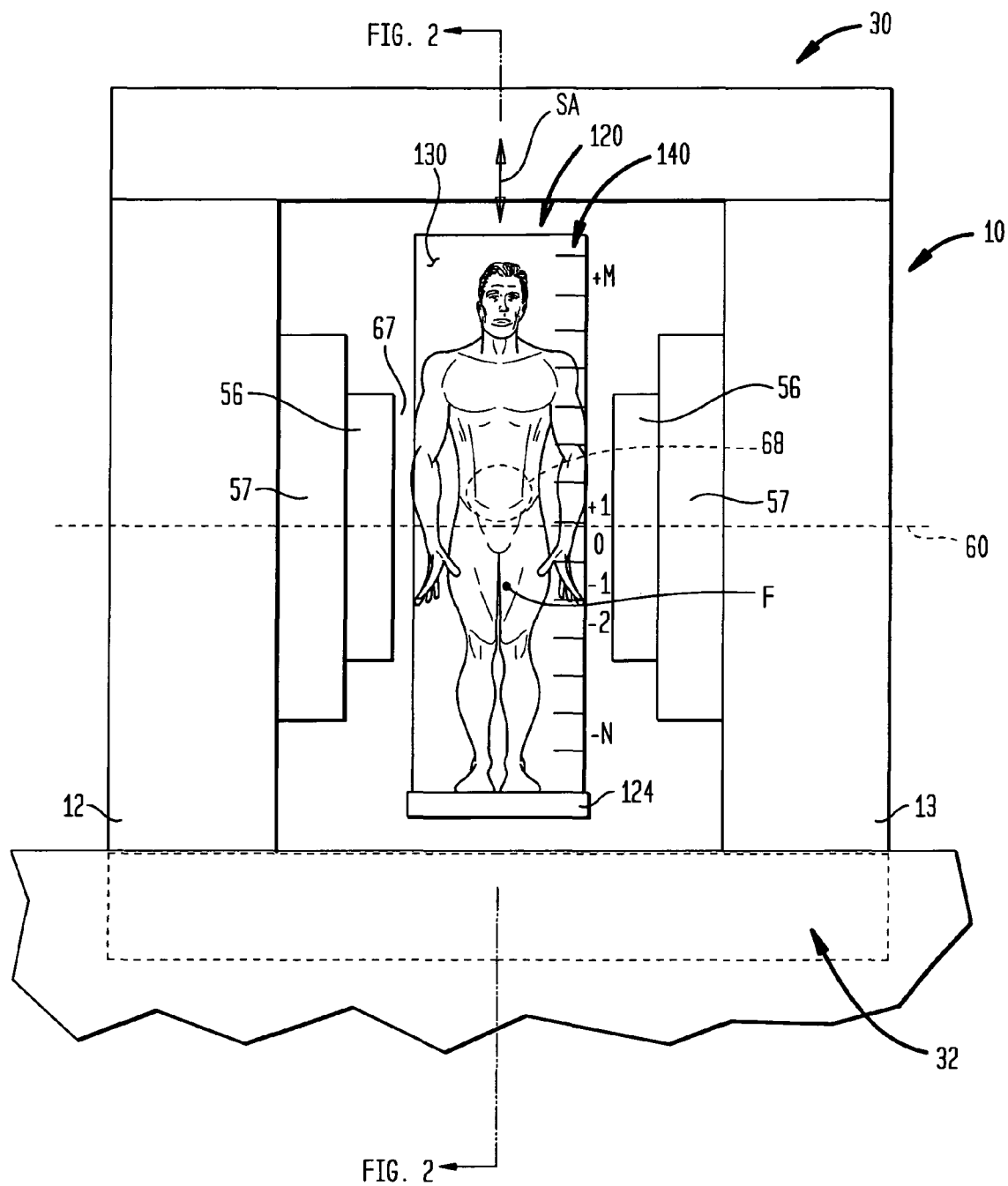
FIG. 1 is a diagrammatic elevational view of apparatus according to one embodiment of the invention in conjunction with a patient.

Apparatus according to one embodiment of the present invention includes a ferromagnetic frame 10. As described in greater detail in the aforementioned '753 patent, the frame 10 is generally in the form of a hollow rectangular solid and includes a top flux return member 30 defining the top wall of the frame, a bottom flux return member 32 defining the bottom wall of the frame and a pair of generally vertical side walls 12 and 13 (FIG. 2) defining the sides of the frame. The frame has large patient entry openings 48 and 50 (FIG. 2) at front and back sides of the frame, i.e., the vertical sides which are not occupied by side walls 12 and 13. The top flux return member 30 defines opening 38 in the top wall of the frame, whereas the bottom flux return member 32 defines an opening 44 in the bottom wall. The frame is maintained above a base structure 104 so that there is a space 111 beneath the bottom of the flux return member communicating with opening 44.

Two cylindrical ferromagnetic poles 56 extend into the interior of the frame from side walls 12 and 13. The poles extend on a common horizontal polar axis or magnetic field axis 60 and define a patient receiving space 67 between them. The apparatus also includes a source of magnetic flux such as electromagnet coils 57 encircling the poles for providing a constant, substantially uniform static magnetic field within an imaging volume 68 in patient-receiving space 67. The imaging volume surrounds field axis 60. The magnet provides a magnetic field having strength and uniformity usable for magnetic resonance imaging within the patient-receiving space, but provides the best, most uniform magnetic field within a particular volume 68, centered on field axis 60.

Figure 2:
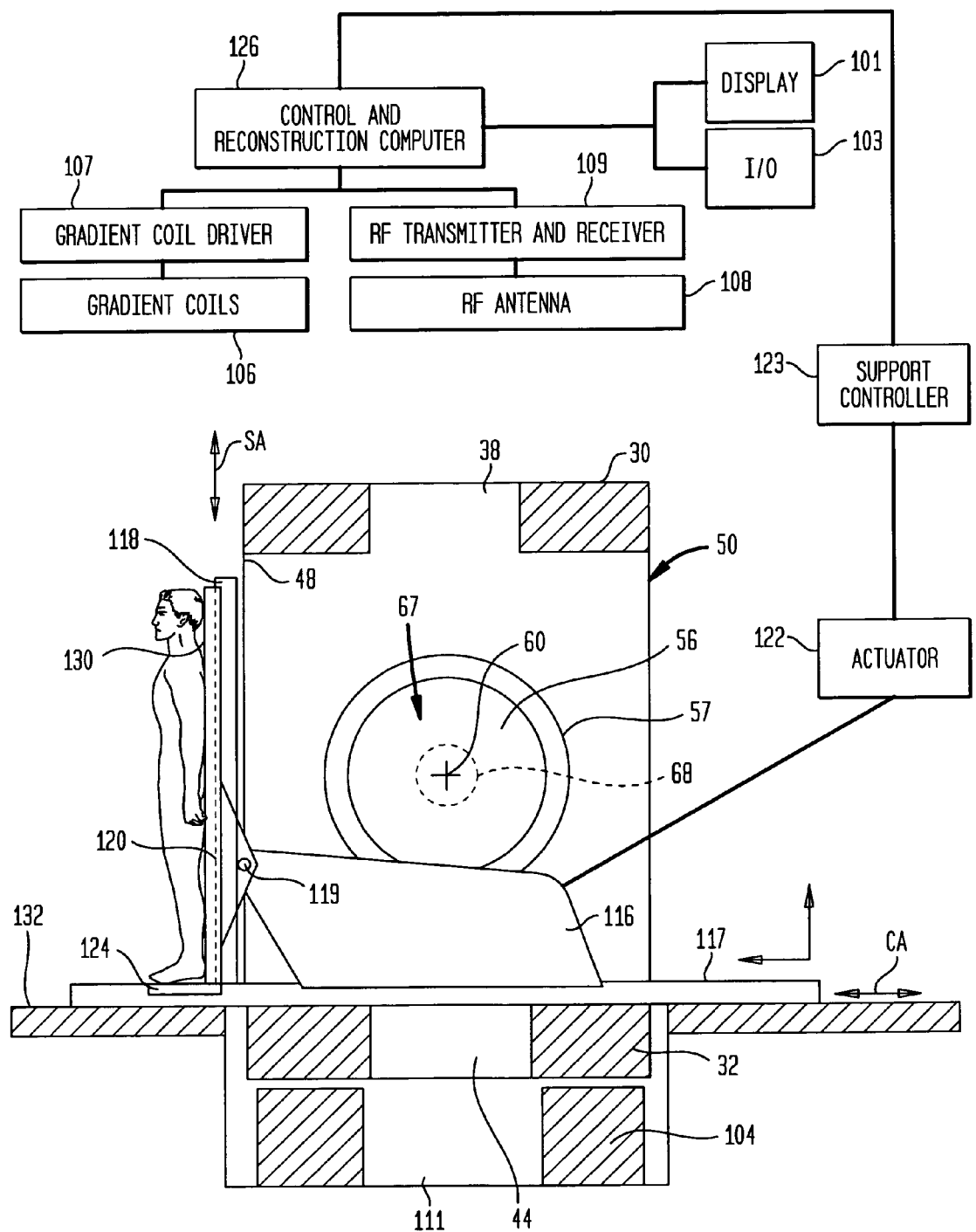
FIG. 2 is a diagrammatic sectional view along line 2-2 in FIG. 1.

A carriage 116 (FIG. 2) is mounted on guides such as rails 117 extending into and out of magnetic frame through the patient entry openings 48 and 50 so that the carriage can move along a carriage axis CA transverse to the field axis (to the right and left as seen in FIG. 2). Rails 117 may be mounted on or embedded in the lower flux return member 32 and the surrounding floor 132 of the building. An elongated support structure 118 is pivotally mounted to the carriage for movement about a horizontal pivot axis 119. An elongated patient support or bed 120 with a footrest 124 at one end is slidably mounted on support structure 118 so that the patient support can move, relative to the support structure 118 and hence relative to pivot axis 119, along a support axis SA in the direction of elongation of the support structure and patient support.

An actuator assembly 122 is provided for driving the carriage along rails 117, for moving the patient support along the support structure 118, and for tilting the support structure about axis 119 relative to the carriage. The actuator assembly may include any devices which can be used to impel mechanical elements relative to one another in a controllable manner. For example, the actuator assembly can incorporate one or more motion sources such as rotary or linear electric motors, pneumatic or hydraulic motors, pneumatic or hydraulic cylinders and the like, and may also include mechanical linkages such as gears, belts, screws, racks, levers, chains, ropes and pulleys connecting each motion source between one or more pairs of elements. The actuator typically also includes control elements such as clutches, switches, valves and brakes responsive to externally-applied control signals. Additionally, the actuator assembly desirably includes feedback elements such as optical or electronic position encoders, switches or mechanical linkages. One set of feedback elements is linked to support structure 118 and patient support 120 for providing signals indicative of the position of the patient support relative to the support structure, whereas a further set of feedback elements is linked to support structure 118 and carriage 116 for providing signals indicative of the angular position of the support structure relative to the carriage. Yet another set of feedback elements provides an indication as to the position of carriage 116 on rails 117. The feedback elements can be directly linked to the support structure, patient support and carriage, or else can be indirectly connected to these elements through intermediate linkages as, for example, through linkages used to transmit motion from the motion source. The individual elements of the actuator assembly can be elements as generally employed in automatic machinery, but most preferably are arranged as disclosed in further detail in co-pending, commonly assigned aforementioned '369 application. Those portions of the actuator assembly, carriage and patient support which extend within the patient-receiving space 67 during operation desirably are formed from non-magnetic materials and do not emit magnetic fields during operation.

A set of gradient coils 106 is physically mounted within the magnet frame. The gradient coils are arranged in the conventional manner to apply magnetic field gradients within the patient-receiving space 67. The gradient coils in turn are connected to a gradient coil driver 107 which is controlled by a computer 126, referred to herein as the control and reconstruction computer. In the conventional manner, the computer 126 can control the gradient coil driver to apply appropriate currents to the various gradient coils so as to provide gradients in any desired direction within patient-receiving space 67 and to vary these gradients with time.

A conventional RF antenna 108 and RF transmitting and receiving apparatus 109 are also associated with the control and reconstruction computer 126. The antenna may include one or more elements positioned within the magnetic frame, on the patient support 120 or carried by the patient's body. The transmitting and receiving apparatus can be actuated by the computer to apply RF excitation signals and to receive the magnetic resonance signals emitted by the patient. The apparatus may use the same or different antenna elements for transmitting and receiving.

Computer 126 is linked to a display 101 such as a CRT display or printer and input/output devices 103 for entry of data and control commands into the computer. The computer includes the conventional elements of a general-purpose computer, including a programmable processor and conventional memory devices for storing data and programs. Control and reconstruction computer is arranged to control the gradient coil driver 107 and the RF transmitter and receiver 109 so as to elicit MRI signals from matter within the patient-receiving space, and to reconstruct an image of such matter from the MRI signals. The techniques of eliciting MRI signals and reconstructing an image therefrom are known in the magnetic resonance imaging art and are not further described herein.

The input/output devices 103 may include conventional elements such as a keyboard, as well as a conventional pointing device such as a mouse, touchpad or trackball, and preferably also include specialized command entry devices such as switches or pushbuttons used to control at least some aspects of the patient movement as discussed below. As disclosed in commonly assigned U.S. patent application Ser. No. 10/301,187, filed Nov. 21, 2002, and entitled "STAND-UP PATIENT HANDLING SYSTEM CONTROL KIOSK," and in the co-pending, commonly assigned U.S. Provisional Patent Application Ser. No. 60/373,964, filed Apr. 19, 2002, and entitled "PATIENT HANDLING SYSTEM CONTROL KIOSK AND CONTROLLER," the disclosures of which are incorporated by reference herein, it is desirable to place at least some of the devices which control movement of the patient support on a panel close to the magnet but spaced from the magnet so that an operator positioned at the control panel can see into the magnet and observe the patient. For example, such a panel can include a "deadman switch," i.e., a button or other element which must be held continually by the operator to enable movement of the patient support.

Actuator assembly 122 is connected to a support controller 123, which in turn is connected to computer 126. The support controller is connected to the control and feedback elements of the actuator. As further discussed below, the support controller is arranged to receive a command from computer 126 directing the support controller to bring the patient support to a particular commanded disposition, and to respond to such command by operating the actuator assembly 122 to drive the carriage relative to rails 117, to move patient support relative to support frame 118, and to pivot the support frame about axis 119 relative to the carriage 116, until the feedback elements of the actuator assembly indicate that the patient support is in the commanded disposition. The support controller may include conventional control elements capable of controlling fixed sequences of operations as, for example, conventional "hard-wired" electrical control apparatus, fluidic, mechanical or electromechanical control devices. Preferably, however, the support controller includes a general-purpose computer with conventional interface devices. For example, where the motion sources included in the actuator include electrical stepper motors, the support controller includes conventional stepper motor interface elements capable of providing electrical power to the stepper motors in response to commands from the processor in the computer. The interface devices in the support controller desirably also include conventional interfaces for receiving signals from the feedback devices in the actuator assembly. Typically, the support controller is arranged to monitor the position of the patient support 120 relative to support structure 118 by counting steps from a known "home" position, and to monitor the position of carriage 116 by counting steps from a home position of the carriage.

The support controller is depicted in FIG. 2 as a structure separate from the control and reconstruction computer 126 but operatively connected to the control and reconstruction computer. In this case, the support controller 123 and the system controller 126 desirably also includes interfaces permitting communication between these two controllers. Alternatively, the support controller 123 may be an integral part of the control and reconstruction computer 126. For example, the processor of computer 126 may perform the logic functions of the system controller. In either case, the support controller 123 desirably also has direct connections to at least some of the input devices 103 as, for example, to a deadman's switch as mentioned above, so that the operator can manually interrupt any movement of the patient support in an emergency. Alternatively or additionally, some of the input devices 103 may be directly connected to elements of the actuator 122. For example, a deadman's switch can be arranged to interrupt power to the actuator so as to stop movement of the patient support in an emergency regardless of any action taken by the support controller 123.

Figure 3:
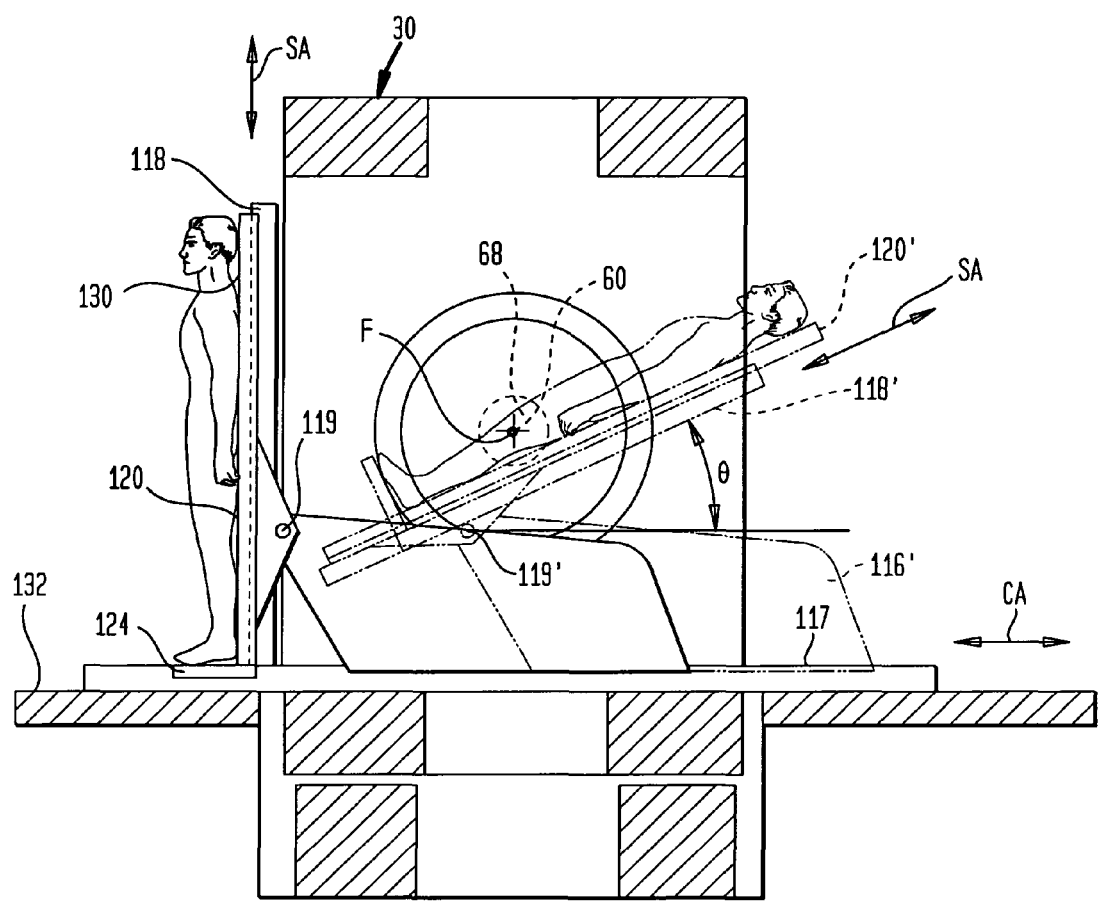
FIG. 3 is a view similar to FIG. 2, but depicting portions of the apparatus in a moved position.

As depicted in FIG. 2, and as also shown in solid lines in FIG. 3, the patient support 120 is in a loading position, with the patient support, and hence the support axis SA extending generally vertically and with the end of the patient support bearing footrest 124 at the bottom, so that footrest 124 is at the bottom of the patient support and hence disposed adjacent the floor 132 of the loading structure and adjacent the guides 117 and bottom flux return member 32 of the magnet. In the load position, patient-receiving surface 130 (the surface adapted to support the patient) of the patient support 120 faces generally in a forward direction, i.e., out of the drawing in FIG. 1 and to the left in FIG. 2. Preferably, the support structure is inclined slightly from an exactly vertical orientation, so that the patient support structure slopes slightly rearwardly (to the right as seen in FIG. 2) towards the top end of the patient support structure. In the particular loading position depicted in FIG. 2, the patient support structure lies just forwardly (just to the left as seen in FIG. 2) of the magnet structure, and just outside of the patient-receiving space 67 within the magnet. In other loading positions, the patient support structure may be in the same orientation but slightly to the rear of the position depicted in FIG. 2, so that the patient support structure is within the patient-receiving space of the magnet. In either case, the patient can be loaded onto the support structure readily simply by walking across the floor, stepping on footrest 124, and leaning against the patient support 120. Auxiliary devices such as belts and straps may be used to restrain the patient in position on the support. In other situations, a different loading position may be used. For example, in the case of a non-ambulatory patient carried on a bed or litter, it is usually desirable to load the patient onto the support while the support is in a horizontal position.

As best seen in FIG. 3, the patient support can be brought to an arbitrary angle θ relative to the horizontal, and can be moved linearly both by (1) moving the carriage 116 along the guide 117 and carriage axis CA, and (2) by sliding the patient support 120 relative to the support structure 118 so as to move the patient support 120 in the direction of the support axis SA. Of course, the orientation of direction SA will depend upon the rotational position of the support structure 118 about pivot axis 119. In the imaging position depicted in FIG. 3 in broken lines, a feature F of the patient's body (toward the top of the patient's leg as depicted) is disposed in alignment with the field axis 60 and hence within imaging volume 68, so that such feature can be imaged in the best manner. The particular imaging position used will vary with the feature to be imaged; a different imaging position would be required to image the patient's head or feet.

Indicia 140 are provided on patient support 120. These indicia form a scale extending in the direction parallel to the support axis SA (FIG. 1). The indicia are arranged so that the zero or datum point of the scale is at a known offset distance in the direction of the support axis from pivot axis 119 when the patient support is in a "home" position, which may be identical to the loading position or different from the loading position. After the patient has been loaded onto the patient support 120, the technician notes the position of feature F in the direction parallel to the support axis SA by reading the indicia. The indicia thus allow the technician to measure the location of the feature F in the frame of reference of the patient support in the direction of support axis SA. This measurement can be taken while the patient support is in the loading position, or, if desired, at any position of the patient support. After taking this measurement, the technician enters the position of the feature as determined by measurements using the indicia into computer 126 using IO devices 103 (FIG. 2). The technician also enters a desired tilt angle θ (FIG. 3) into computer 126 through the IO devices. Computer 126 responds to this information by calculating the required position of carriage 116 in the carriage direction CA and the required position of the patient support 120 relative to support structure 118 in the direction parallel to support axis SA, which will place the feature F in alignment with the field axis 60. Together with the desired tilt angle θ, which specifies the rotational position of the support structure 118 and patient support about pivot axis 119, these positions constitute a set of coordinates fully specifying the required imaging position.

Because pivot axis 119 lies at a fixed vertical elevation, the height H of the field axis 60 above the pivot axis is fixed and known. For the feature F to be aligned with the field axis 60:

$$D_{SAF} \sin \theta = H - O_F \cos \theta \quad (1)$$

or, rearranging:

$$D_{SAF} = (H - O_F \cos \theta)/\sin \theta \quad (2)$$

where:
  θ is the specified tilt angle;
  $O_F$ is the offset distance between feature F and a theoretical plane 140 passing through the pivot axis 119 and extending parallel to the support axis SA; and
  $D_{SAF}$ is the distance in the direction of the support axis SA between the pivot axis 119 and feature F.

The offset distance $O_F$ is equal to the sum of the fixed distance $O_{130}$ between the pivot axis 119 and the exposed or patient bearing surface 130 of the patient support 120, and the thickness $O_B$ of that portion of the patient's body lying between surface 130 and the feature. For most anatomical features of a typical adult patient lying recumbent on surface 130, with his or her posterior or anterior surface abutting surface 130, reasonable alignment of the feature F with the field axis can be obtained by assuming that $O_B$ is a fixed distance, most preferably about 16.5 cm. Given that assumption, the offset distance $O_F$ is also known. Thus, given the specified rotational coordinate or tilt angle θ, the computer calculates $D_{SAF}$ directly using equation (2).

The required travel T of the patient support 120 relative to support structure 118 in direction SA from the home position of the patient support is given by:

$$T = D_{SAF} - SR_F + SR_{DATUM} \quad (3)$$

where:
  $SR_F$ is the scale reading of the feature F; and
  $SR_{DATUM}$ is the scale reading of a datum point on the patient support, i.e., the point on the patient support that is aligned with the pivot axis when the patient support is in its home position.

For feature F to be aligned with field axis 60 in the horizontal direction parallel to the carriage axis CA, the pivot axis 119 must be disposed at a location $D_{CA}$ given by:

$$D_{CA} = D_{SAF} \cos \theta - O_F \sin \theta \quad (4).$$

Because the pivot axis 119 is fixed to the carriage, the carriage axis coordinate $D_{CA}$ of the pivot axis translates directly into carriage position in the direction of the carriage axis. If the home position of the carriage is selected so that the pivot axis lies directly beneath the field axis in the home position, then the required travel of the carriage from the home position is simply equal to $D_{CA}$. If not, $D_{CA}$ can be converted to carriage travel by subtracting or adding a fixed offset.

The calculations above use sine and cosine functions. Similar calculations can be performed using linear approximations of the sine and cosine functions. Also, in a system which uses position encoders to monitor the positions of the carriage and patient support, the travel distances from home position for the patient support and for the carriage typically are converted into the corresponding encoder count values by dividing each travel distance by the number of encoder counts per unit distance.

Once the computer has calculated the coordinates and required travel from home position, it may command the support controller 123 and the actuator or drive mechanism 122 to move the carriage along the carriage axis, tilt the support structure 118 and patient support 120 to the specified rotational position θ, and slide the patient support 120 relative to support structure 118 to the required support axis location. The computer may give the commands to perform all of these required motions simultaneously or sequentially.

In a sequential system, it is desirable to bring the patient support to the required rotational position or tilt angle θ before moving the patient support 120 in the support axis direction. For example, as seen in FIG. 3, the patient support, in the imaging position, is extended upwardly relative to the patient support. If this extension was accomplished before tilting and before retracting the carriage 116 rearwardly to position 116', the extended patient support could interfere with the top flux return member 30. Most preferably, the computer, support controller, and actuator are arranged so that movement of the carriage 116, tilting of the support structure 118, and sliding of the patient support 120 relative to the support structure can occur only while the technician is holding the deadman switch incorporated in the input/output devices.

Thus, the system brings the patient support from the load position to the required imaging position readily, without trial and error manipulation by the technician. This assures that the feature of the patient is properly aligned at or at least near field axis 60, and hence disposed within the imaging volume 68. Once the patient support is in the required imaging position, images can be acquired in the conventional manner.

As disclosed in co-pending, commonly assigned U.S. patent application Ser. No. 10/419,385 [092 II], the computer 126 and support controller may be arranged to move the patient support through a series of plural imaging positions in different orientations and hence at different tilt angles. As discussed in greater detail in the '385 application, the computer may acquire an image data set defining an image of the patient in each such orientation and may automatically compare these image data sets to highlight anatomical changes occurring with patient reorientation.

As also disclosed in the '385 application, the computer 126 may be arranged to adjust the magnetic field gradients depending on the orientation or rotational position of the support, so that the field gradients always have a constant orientation relative to the patient support, even as the orientation of the patient support relative to the magnet changes.

The discussion above concerning the use of indicia 140 to measure the position of feature F in the direction parallel to the support axis SA by reading the indicia does not imply that the technician must determine the position in as a numerical value. As used in this disclosure, the term "measure" should be understood as merely denoting the operation of obtaining information from which the position can be deduced. For example, the indicia may have arbitrary letter or color designations associated with them, rather than the numerical designations (+M . . . +1, 0, −1, −2 . . . −N) shown in FIG. 1. Provided that the computer stores information associating the arbitrary designation associated with each indicium and a position, the technician need only select the indicium closest to the feature F and enter its arbitrary designation, which the computer then translates into position.

Figure 5:
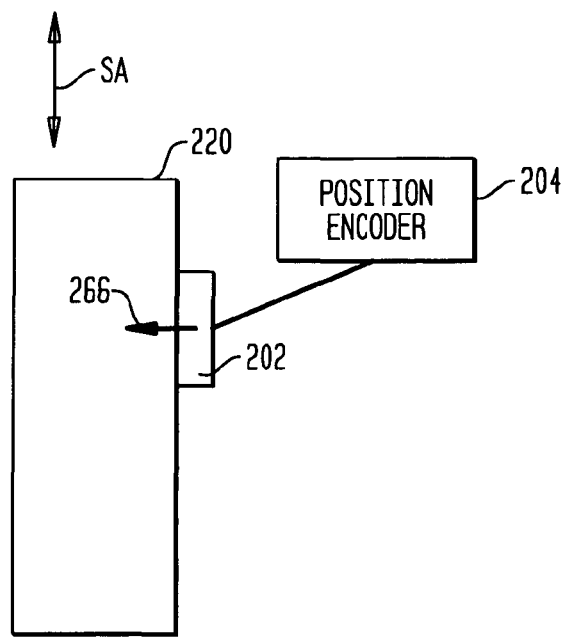
FIG. 5 is a block diagram depicting portions of apparatus according to a further embodiment of the invention.

The measuring device used to acquire the location of the patient's body feature need not include a scale, but instead, can include an element 202 (FIG. 5) which is slidably mounted to the patient support 220 for movement relative to the patient support 220 in the direction parallel to support axis SA and linked to a mechanical, electrical, optical, or other position encoder operative to detect the position of element 202 in the direction of the support axis SA. The position encoder may be arranged to input a position value representing the position of element 202 directly into the computer in response to a signal entered by the technician. Element 202 is provided with a physical pointer 206 or an analogous device such as a laser beam. The technician can bring element 202 to a position where the pointer 206 or laser beam is aligned with the feature of the patient to be imaged and then enter a signal, as by pressing a button included in I/O devices 103, to indicate that the element has been aligned. The computer inputs the position value from encoder 204. The position value acquired by use of element 202 and position encoder 204 is used in exactly the same way as the position value acquired using indicia 140 (FIG. 1).

Figure 6:
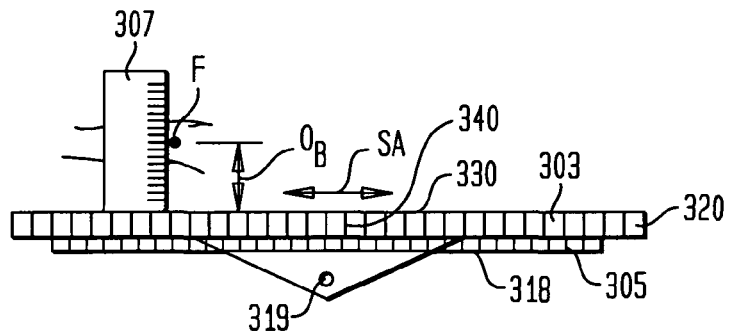
FIG. 6 is a diagrammatic elevational view depicting a portion of the apparatus according to a further embodiment of the invention.

As seen in FIG. 6, indicia 340 forming a scale extending in the support axis direction SA may be provided on an edge surface 303 of the patient support. Such indicia can be used instead of indicia on the front surface 330, or in addition to indicia on the front surface. In a further variant, the support structure 318 may be provided with indicia 306 defining a scale extending in the support axis direction. These indicia may be used instead of indicia on the patient support itself. In such an arrangement, the computer 126 is arranged to add an offset value to the scale readings taken using indicia 305 on the support structure. This offset value represents the displacement of the patient support relative to support structure 318 from its home position at the time the scale reading is taken. In a further variant, the computer may be arranged to bring the patient support to its home position or other known location relative to the support structure prior to reading the scale on the support structure. Similarly, a sliding element such as element 202 discussed above with reference to FIG. 5 may be mounted on the support structure 318 rather than on the patient support 320 itself.

Figure 4:
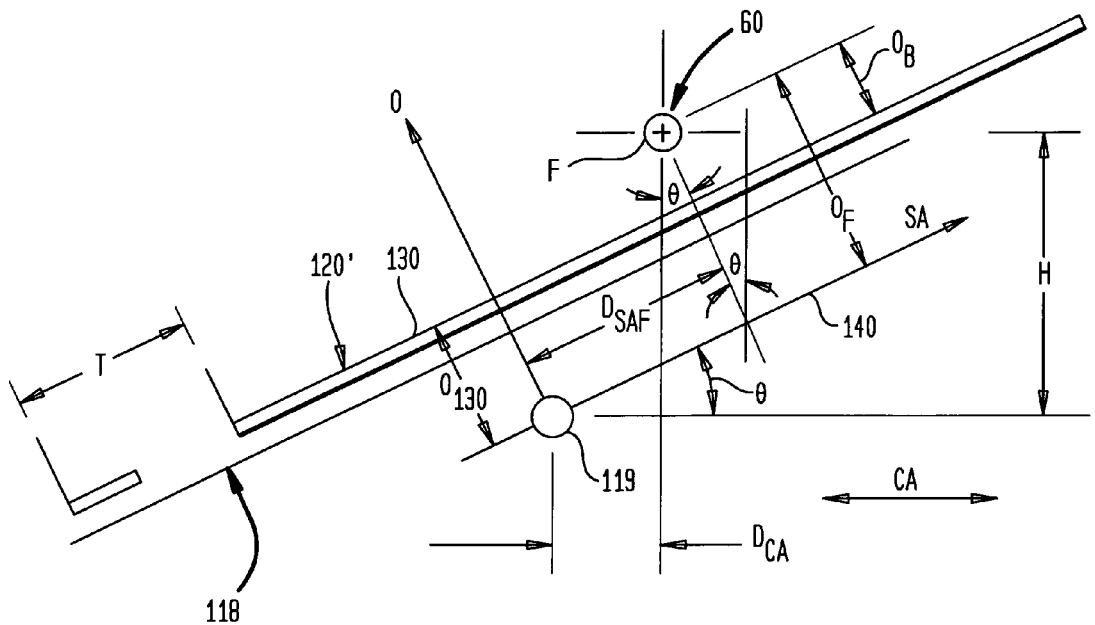
FIG. 4 is a schematic view depicting a coordinate system utilized in the apparatus of FIGS. 1-3.

In the arrangements discussed above, the offset distance $O_F$ (FIG. 4) is assumed, based on an assumed value of the distance $O_B$ between the surface of the patient support and the feature to be imaged. In a further variant, that distance can be measured, as, for example, by a separate distance measuring device such as a ruler or square 307 (FIG. 6) placed on the patient-supporting surface 330, or otherwise mechanically engaged with the patient support 320 or support structure 318. The measured offset distance $O_B$ may be added to the fixed component $O_{130}$ (FIG. 4) to give a total offset distance $O_F$ between the feature F and the pivot axis 319 in the offset direction perpendicular to the support axis direction and perpendicular to the pivot axis. In a further variant, the scale 307 or other measuring device may be calibrated to give the value of $O_F$ directly. In either case, the measured value is input into computer 126 by the technician. In yet another variant, measuring device 307 may include a slidable element and position encoder or other form of transducer connected to the computer so that the value can be entered automatically.

Figure 7:
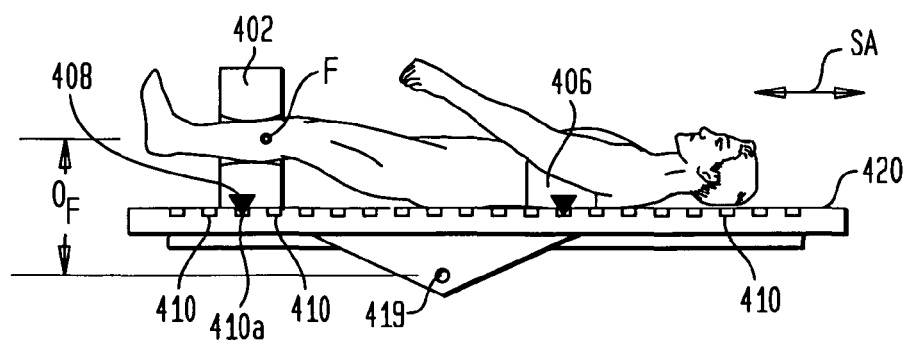
FIG. 7 is a view similar to FIG. 6, but depicting a portion of apparatus according to yet another embodiment of the invention.

As seen in FIG. 7, one or more fixtures 402, 406 may be mounted to the patient support for support various elements of the patient's anatomy. Where the feature F to be imaged is supported by such a support, the offset distance $O_F$ may depend on the structure of the fixture. For example, fixture 402 is a ring-like fixture arranged to hold a patient's leg within a bore. The mechanical configuration of the fixture is such that the center of the bore lies at a known offset distance $O_F$ from the pivot axis 419. Thus, when the feature F to be imaged is a feature held within this bore, it can be assumed that the feature F lies at this known offset distance. Similarly, fixture 406 is a rest which holds an arm in an elevated position also having a known offset distance $O_F$. As disclosed, for example, in co-pending commonly assigned U.S. patent application Ser. Nos. 10/131,843, and 10/427,443, the disclosures of which are incorporated by reference herein, and in the aforementioned '369 application, numerous fixtures can be provided and may be affixed to the patient support. These fixtures may or may not include RF coils used in the imaging process. The offset distance $O_F$ associated with each fixture may be stored in a memory accessible by computer 126 so that the proper offset distance can be selected by the computer automatically in response to entry of data by the technician indicating that a particular fixture is in use. In yet another variant, the system may include sensors (not shown) for detecting the presence of a particular fixture and setting the offset distance $O_F$ automatically. Such sensors may include, for example, devices for reading the identity of the fixture; or the proper offset distance, from a memory mounted on the fixture; or a bar code reader; or RFID tag reader operative to read a tag attached to the fixture.

As disclosed in the aforementioned applications, a positioning fixture can be arranged so that the fixture can be mounted in a plurality of discrete locations along the lengthwise or support axis dimension of the patient support. For example, the fixture or a mounting device used to hold the fixture may be arranged to engage any one of a plurality of sets of holes or other discrete mounting features arrayed along the length or support axis dimension of the patient support. For example, as seen in FIG. 7, fixture 402 has a projection 408, and patient support 420 has a plurality of holes 410 arrayed along its support axis dimension. Projection 408 is engaged in one of these holes 410a. Accordingly, fixture 402 is disposed at a position along the support axis associated with hole 410a. Thus, the position of the feature F can be taken as equal to the position of hole 410a. The position measuring device used to determine the position of the feature F thus may include the holes. Indicia may be provided adjacent each set of holes, and the technician may enter that identity into the computer. The computer may look up the identity of the set of mounting features which is entered into the computer.

In a further variant, the fixture 402 may be arranged to position the feature F at a position which is offset in the support axis direction from the mounting feature, as, for example, at a predetermined distance in the support axis direction from hole 410a. The computer may add the predetermined space and distance associated with the fixture to the support axis position associated with the mounting feature. Here again, different predetermined spacing distances may be associated with different fixtures in the same manner as discussed above with reference to the offset distance.

In yet another variant, sensors may be provided on the patient support for detecting engagement of a fixture with a particular one or ones of the mounting features, so that the support axis location is automatically entered into the computer based upon engagement of the fixture with a particular set of mounting features.

Figure 8:
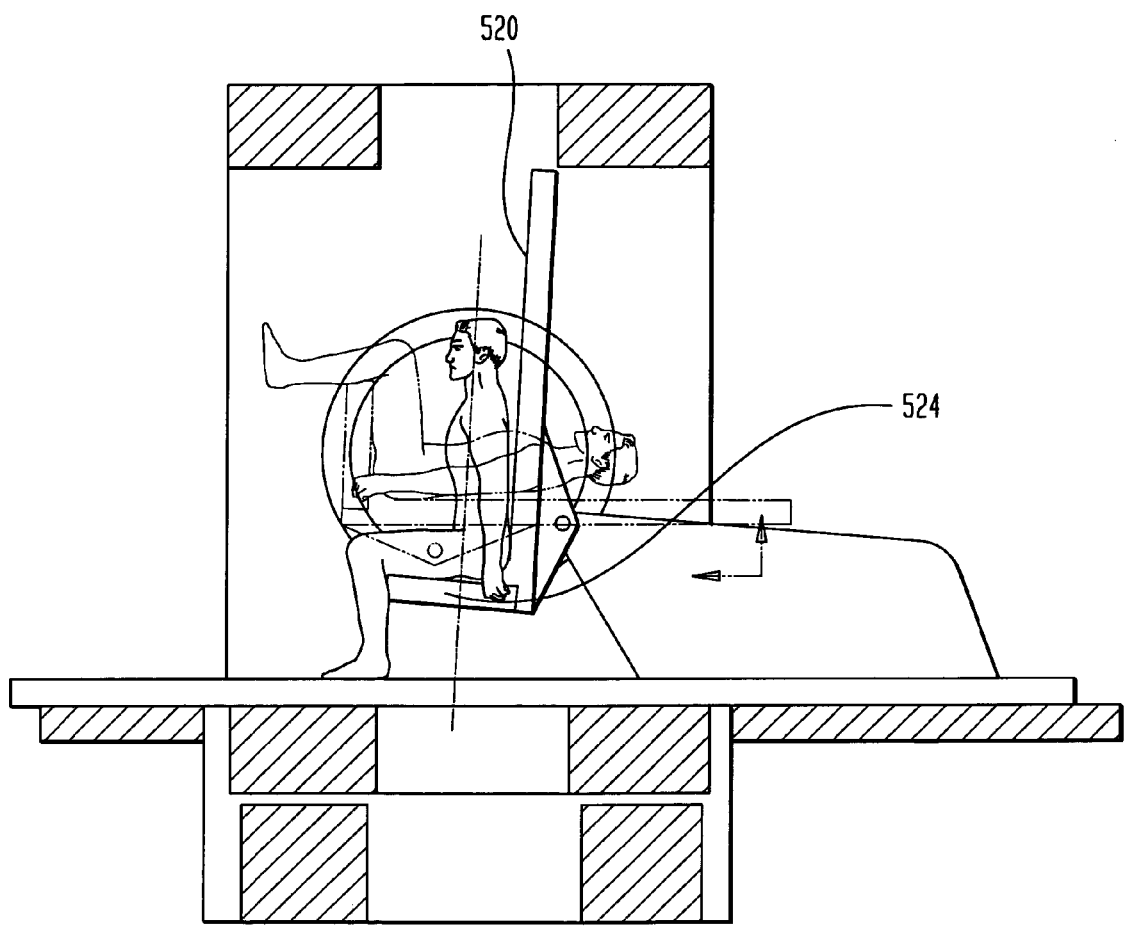
FIG. 8 is a diagrammatic sectional view similar to FIG. 2, but depicting portions of apparatus according to yet another embodiment of the invention.

As seen FIG. 8, the patient support 520 may be provided with a seat 524 instead of, or in addition to the footrest discussed above, so that the patient may be placed in a seated posture on the patient support. A seat constitutes a particular example of a fixture. The appropriate offset distance OF for use with the seat will depend on the particular feature of the patient to be imaged. Thus, if the feature is the patient's lower leg or knee, the offset distance will be relatively large; whereas, if the feature is a feature of the patient's torso or head, the offset distance will be the same as that used for a patient lying in contact with the patient support 520 as discussed above. In other respects, operation of the system with a seated patient is the same as discussed above.

Figure 9:
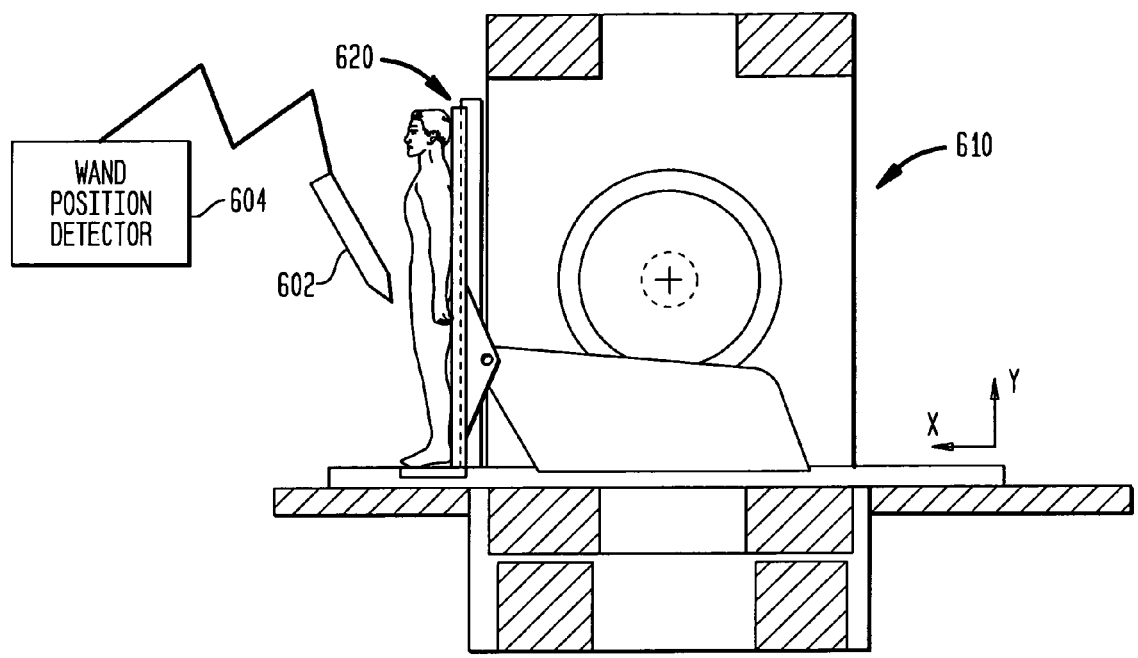
FIG. 9 is a further sectional view similar to FIG. 2, but depicting a portion of apparatus according to yet another embodiment of the invention.

In a further variant (FIG. 9), the position measuring device may include a wand 602 and a wand position detector 604 adapted to detect the position of wand 602 in a frame of reference which may be the frame of reference of the magnet 610 or the frame of reference of the patient support 620. Numerous systems for detecting the position of a wand or other object in space are known. Some of these systems use optical components; others detect the position and orientation of the object by detecting properties of a magnetic field passing through the object; and still other systems of this type use mechanical linkages connected between the wand and a reference point. This magnetic field may be a field generated by magnet 610 and/or by the gradient coils 106 (FIG. 2), or some combination of these. Here again, the technician positions wand 602 so that the point of the wand lies on the feature to be imaged and signals the computer to acquire the position of the wand. If the wand position is acquired in the frame of reference of the patient support 620, the wand position can be converted to data such as the support direction position and offset distance of the feature from the pivot axis, and these may be used in the same manner as discussed above. Alternatively, if the wand system is arranged to determine the position of the wand, and hence the position of the patient's feature to be imaged, in the frame of reference of the magnet, that information can be converted back into position of the feature in the frame of reference of the patient support, provided when the patient support is in a known position, as, for example, the loading position discussed above, at the time the wand position is acquired. Stated another way, provided that the patient support is in a known position in the frame of reference of the magnet, the transformation between position in the frame of reference of the magnet and position in the frame of reference of the patient support can be computed using known techniques for transformation of coordinate systems.

Figure 10:
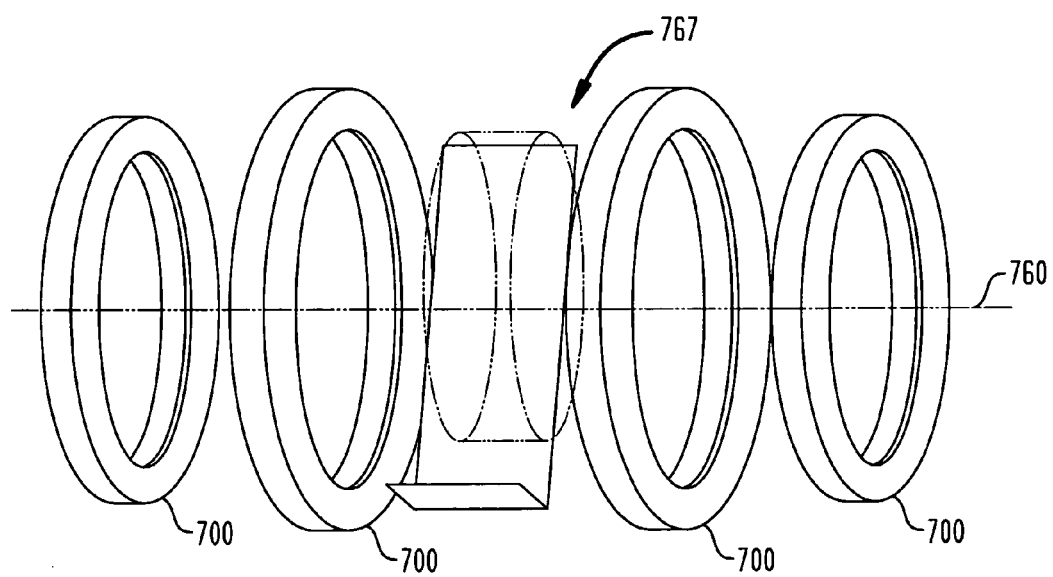
FIG. 10 is a diagrammatic perspective view showing portions of apparatus according to yet another embodiment of the invention.

In the embodiments discussed above, the pole structures of the magnet are ferromagnetic poles. However, this not essential; the pole structures include coils 700 (FIG. 10) aligned along the field axis 760 and defining the patient-receiving space 767 between these coils.

In the embodiments discussed above, the field axis is horizontal and the pivot axis is also horizontal. In other arrangements, the field axis may be vertical, and the pivot axis also is vertical. For example, as shown in U.S. Pat. No. 6,496,007, the disclosure of which is incorporated by reference herein, a patient support may be arranged to pivot about a vertical axis relative to a supporting table or carriage, and the patient support is also arranged to slide relative to the pivot axis in horizontal directions. The present invention can be applied to calculation of coordinates for such a patient support, and can be used to move such a support automatically in the manner discussed above.

Figure 11:
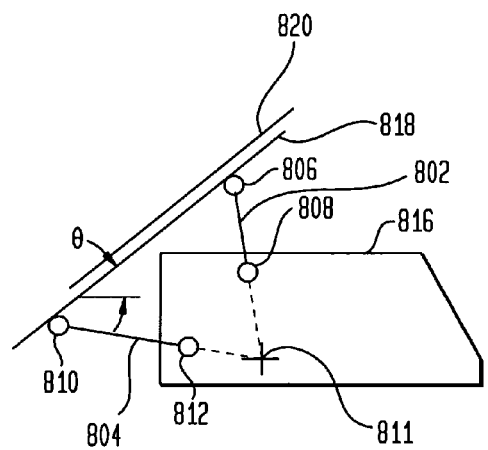
FIG. 11 is a diagrammatic view depicting portions of a system in accordance with yet another embodiment of the invention.

In the embodiments discussed above, the pivot axis is disposed in a fixed position relative to the carriage and defined by a shaft or other simple pivot joint at the pivot axis. However, other forms of pivoting connections can be used. For example, as seen in FIG. 11, the support structure 818 and patient support 820 are pivotally connected to carriage 816 by a first set of links 802 and second set of links 804. Links 802 are rotatably connected to support structure 818 at a first pin joint 806, and rotatably connected to carriage 816 at a second pin joint 808. Similarly, links 804 are connected to support structure 818 at a first pin joint 810 and at a second pin joint 812. Such an arrangement is commonly referred to a "four-bar" linkage, in which the bars of the linkage include the patient support, the carriage, and bars 802 and 804. In such a four-bar linkage, the patient support 818 can pivot relative to carriage 816 about an instantaneous pivot axis 811. However, the support structure 818, and hence the patient support 820, may still be considered as pivotally connected to the carriage. Other, more complex linkages which permit pivoting may also be employed. If the pivoting motion includes movement of the pivot axis, the calculations discussed above must be modified to take account of such motion, i.e., the height of the pivot axis will depend on the desired rotational position θ in known and readily calculable manner.

Figure 12:
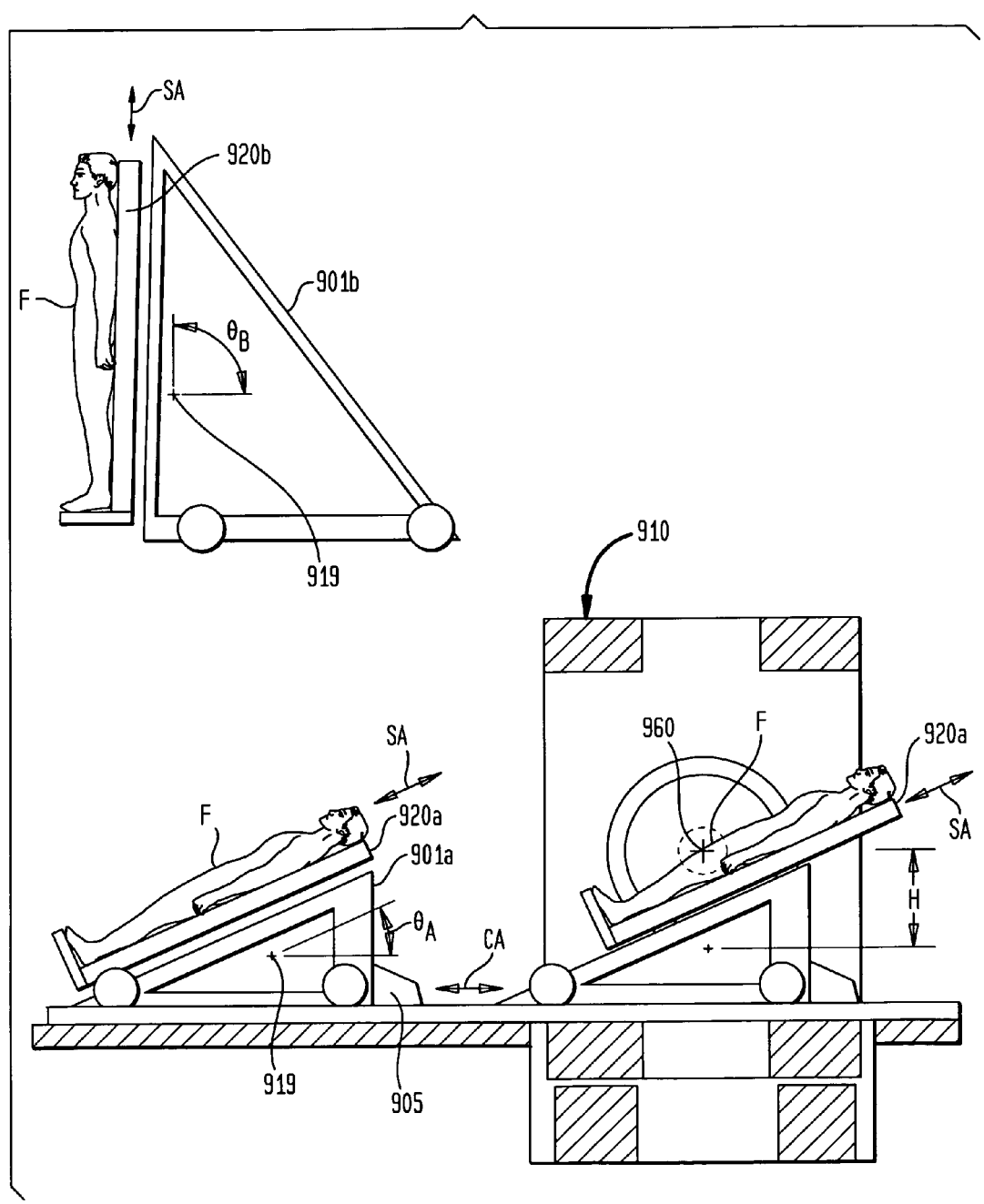
FIG. 12 is a diagrammatic view depicting portions of a system in accordance with yet another embodiment of the invention.

In the embodiments discussed above, the patient support is rotatable about a pivot axis, so that the patient can be brought to any desired rotational position about the pivot axis. In the embodiment of FIG. 12, a plurality of patient supports 920 are provided. Each patient support is arranged to position a patient in a particular patient orientation, i.e., a particular rotational position about an imaginary reference axis 919. Axis 919 extends parallel to the field axis 960 at a predetermined height H below the field axis of the magnet when the support is associated with the magnet. For example, patient support 920a is mounted to a frame 901a which holds the support in a reclined position, so that the patient support and hence the support axis SA extend at a relatively small angle $\theta_A$ to a horizontal plane. Patient support 920b is mounted to a frame 901b which holds the support, and hence the support axis, in a more upright position, at a relatively large angle $\theta_B$ to the horizontal plane. Each patient support is movable along the support axis relative to its frame and hence relative to the reference axis 919. Each frame and patient support includes a drive mechanism (not shown) for moving the patient support relative to the frame and reference axis in the support axis direction SA. Other patient supports (not shown) and their associated frames are arranged similarly, but with different predetermined angles θ. Thus, a patient can be positioned in any one of various orientations by selecting an appropriate patient support, loading the patient onto such support and bringing the support into association with the magnet 910.

Each frame, and hence the associated support, is movable relative to magnet 910 and field axis 968 in a along a carriage axis CA transverse to the field axis. In the particular embodiment illustrated, each frame is equipped with wheels 903 which engage rails 917 extending in the carriage axis direction. A fixture such as an abutment 905 is mounted for movement along the rails 917, and provided with a latch mechanism (not shown) for temporarily connecting the frame of the particular support which is in use to the abutment. Abutment 905 is connected to an actuator (not shown) capable of driving the abutment, and hence the support which is in use, to a desired position along the carriage axis. Alternatively, each frame may be provided with features which can engage a separate carriage (not shown) which is movable along the rails or otherwise movable in the carriage axis direction.

In this embodiment, the problem of calculating an appropriate support axis location and carriage axis location to place a feature F in the imaging volume is similar to that discussed above. Here again, the support axis location and carriage axis location can be determined based upon the position of the feature F relative to the support and the rotational position θ of the support axis SA. The calculations are essentially the same as those discussed above. For example, the support axis location and carriage axis location of support 920a to place feature F in alignment with the field axis (as shown at 920a' in FIG. 12) is different than the support axis location and carriage axis location required to place the same feature F in alignment with the field axis when the patient is disposed on support 920b.

In this embodiment, the technician may determine the position of the feature in exactly the same way as discussed above, and may enter the measurement along with the predetermined rotational position into the computer in the same way as discussed above. Alternatively, the technician or an automatic device may input the identity of a particular patient support and frame, and may look up the predetermined rotational position associated with that support and frame in a lookup table. The computer calculates the support axis and carriage axis locations, and actuates the drive mechanisms to position the patient support and patient.

The disclosure of U.S. Pat. No. 6,677,753 is hereby incorporated by reference herein.

As these and other variations and combinations of the features discussed above can be utilized without departing from the invention as defined by the claims, the foregoing description of the preferred embodiments should be taken by way of illustration rather than by way of limitation of the invention as defined by the claims.

The invention claimed is:

1. A magnetic resonance imaging system comprising:
   (a) a magnet defining a patient-receiving space and an imaging volume within said patient-receiving space;
   (b) a patient support, said patient support being pivotable about a pivot axis through a range of rotational locations and movable relative to said pivot axis along a support axis transverse to said pivot axis through a range of support-axis locations, said patient support being movable along said support axis separately from pivoting motion of the patient support about said pivot axis when said support is in any rotational location within said range of rotational locations;
   (c) a locating device configured to determine a position of a feature of a patient's body while the patient is supported on said patient support; and
   (d) a computer configured to calculate a set of locations including rotational and support-axis locations for an imaging position at which said feature of the patient's body is disposed within said imaging volume based at least in part on the position of said feature determined by said locating device.

2. The system of claim 1 wherein said locating device is arranged to determine the position of said feature relative to said patient support.

3. The system of claim 2 wherein said locating device is arranged to determine the position of said feature relative to said patient support in a direction parallel to said support axis.

4. The system of claim 3 wherein said computer is operative to calculate said set of locations based in part on an assumed location of said feature of the patient relative to the pivot axis in an offset direction perpendicular to said pivot axis and perpendicular to said support axis.

5. The system of claim 3 wherein said support includes an elongated platform extending in said support direction.

6. The system of claim 5 wherein said locating device includes indicia mounted adjacent said platform defining a scale extending parallel to support axis.

7. The system of claim 5 wherein said pivot axis is substantially horizontal.

8. The system of claim 7 wherein, when said support is in a loading position, said elongated platform extends generally vertically.

9. The system of claim 8 wherein said support includes a foot rest and said foot rest is disposed near the bottom of the platform when said support is in said rest position.

10. The system of claim 1 further comprising a carriage, said patient support being pivotably connected to said carriage for rotation relative to said carriage about said pivot axis, said carriage being movable relative to said magnet along a carriage axis transverse to said pivot axis through a range of carriage axis locations, said set of locations derived by said computer including a carriage location along said carriage axis for said imaging position.

11. The system of claim 10 wherein said magnet defines a horizontal field axis and said pivot axis is generally parallel to said horizontal field axis.

12. The system of claim 11 wherein said carriage direction is a horizontal direction transverse to said horizontal field axis.

13. The system of claim 10 further comprising one or more drive mechanisms adapted to actuate said pivoting movement, movement of said support along said support axis, and movement of said carriage in along said carriage axis, said computer being connected to said one or more drive mechanisms and operative to command said one or more drive mechanisms to move said support to said imaging position.

14. The system of claim 1 further comprising one or more drive mechanisms adapted to actuate said pivoting movement and movement of said support along said support axis, said computer being connected to said one or more drive mechanisms and operative to command said one or more drive mechanisms to move said support to said imaging position.

15. The system of claim 1 wherein said computer is operative to calculate said locations based in part on a specified orientation of said support so that said support in said imaging position has said specified orientation.

16. The system of claim 1 wherein said locating device is operative to locate said feature of said patient in the frame of reference of the magnet while said support is in a known position and said computer is operative to determine said rotational and support-axis locations of said patient support in said imaging position based upon the measured position of the feature and the rotational and support direction locations of said patient support in said known position.

17. The system as claimed in claim 16 wherein said locating device includes a pointer and means for determining the position of the pointer while the pointer is disposed adjacent the feature of the patient.

18. A magnetic resonance imaging system comprising:
   (a) a magnet defining a patient-receiving space and an imaging volume within said patient-receiving space;
   (b) a patient support, said patient support being pivotable about a pivot axis through a range of rotational locations and movable relative to said pivot axis along a support axis transverse to said pivot axis through a range of support-axis locations;
   (c) a locating device arranged to determine a position of a feature of a patient's body relative to said patient support while the patient is supported on said patient support; and
   (d) a computer arranged to calculate a set of locations including rotational and support-axis locations for an imaging position at which said feature of the patient's body is disposed within said imaging volume based at least in part on the position of said feature determined by said locating device;
   wherein said locating device is arranged to determine the position of said feature relative to said patient support in a direction parallel to said support axis, and wherein said locating device is operative to determine the location of said feature relative to the pivot axis in an offset direction perpendicular to said pivot axis and perpendicular to said support axis, and wherein said computer is operative to calculate said set of locations based in part on said determined location in said offset direction.

19. A magnetic resonance imaging system comprising:
(a) a magnet defining a patient-receiving space and an imaging volume within said patient-receiving space;
(b) a patient support, said patient support being pivotable about a pivot axis through a range of rotational locations and movable relative to said pivot axis along a support axis transverse to said pivot axis through a range of support-axis locations;
(c) a locating device arranged to determine a position of a feature of a patient's body relative to said patient support while the patient is supported on said patient support; and
(d) a computer arranged to calculate a set of locations including rotational and support-axis locations for an imaging position at which said feature of the patient's body is disposed within said imaging volume based at least in part on the position of said feature determined by said locating device;
wherein said locating device is arranged to determine the position of said feature relative to said patient support in a direction parallel to said support axis, and wherein said locating device includes at least one fixture mountable on the patient support for supporting the feature of the patient at a known location of said feature relative to the pivot axis in an offset direction perpendicular to said pivot axis and perpendicular to said support axis, and wherein said computer is operative to calculate said set of locations based in part on said known location in said offset direction.

20. The system of claim 19 wherein said at least one fixture includes a plurality of fixtures each having an associated known location in said offset direction, and wherein said computer is operative to select the known location in said offset direction based on information as to the particular fixture mounted to said support.

21. A method of positioning a patient for magnetic resonance imaging comprising the steps of:
(a) loading a patient on a patient support while the patient support is disposed in a load position;
(b) specifying an imaging position for the patient support by measuring a position of a feature of the patient's body after said loading step and automatically calculating a set of locations defining an imaging position based at least in part on said measured position so that movement of the support to said imaging position will align said feature of the patient's body with the field axis; and
(c) moving the patient support from said load position to said imaging position by:
(i) rotating the patient support about a pivot axis parallel to the field axis;
(ii) moving the patient support linearly relative to the pivot axis along a support axis transverse to the pivot axis; and
said step of specifying an imaging position including specifying a rotational position within a range of rotational positions and a support-axis position.

22. The method as claimed in claim 21 wherein said patient support is mounted to a carriage defining said pivot axis, said step of moving the patient support includes moving the carriage and the pivot axis relative to the magnet along a carriage axis transverse to said field axis, said step of specifying an imaging position including specifying a carriage-axis position.

23. The method as claimed in claim 22 wherein said step of moving the carriage includes moving the carriage on guides extending parallel to said carriage axis.

24. The method as claimed in claim 22 wherein said movement steps include performing (i) and (ii) at least partially simultaneously.

25. The method as claimed in claim 24 wherein said measuring step includes measuring the position of the feature in the frame of reference of the patient support.

26. The method as claimed in claim 24 wherein said reference position is said load position.

27. The method as claimed in claim 24 wherein said reference position is different from said load position.

28. A magnetic resonance imaging system comprising:
(a) a magnet defining a patient-receiving space and an imaging volume within said patient-receiving space;
(b) one or more patient supports, said one or more patient supports being configured to provide a plurality of different predetermined rotational positions about a reference axis during imaging, each said patient support being movable along a support axis transverse to said reference axis through a range of support-axis locations;
(c) a locating device configured to determine a position of a feature of a patient's body while the patient is supported on one of said one or more patient supports; and
(d) a computer configured to calculate a set of locations including a support-axis location for an imaging position at which said feature of the patient's body is disposed within said imaging volume based at least in part on the position of said feature determined by said locating device and on the predetermined rotational position provided by said one of said one or more patient supports.

29. The system of claim 28 wherein said one or more patient supports include a plurality of patient supports, different ones of said plurality of patient supports being configured to provide different predetermined rotational positions about said reference axis.

30. The system of claim 29, wherein each said patient support is movable relative to said magnet along a carriage axis transverse to said reference axis through a range of carriage axis locations, said set of locations derived by said computer including a carriage location along said carriage axis for said imaging position.

31. The system of claim 30 wherein said magnet defines a horizontal field axis and said reference axis is generally parallel to said horizontal field axis.

32. The system of claim 31 further comprising one or more drive mechanisms adapted to actuate movement of said support along said support axis, and movement of each said patient support along said carriage axis, said computer being connected to said one or more drive mechanisms and operative to command said one or more drive mechanisms to move one said patient support having a patient positioned thereon to said imaging position.

* * * * *